(12) United States Patent
Bergmann et al.

(10) Patent No.: US 8,026,374 B2
(45) Date of Patent: Sep. 27, 2011

(54) PROCESS FOR PREPARING (METH)ACRYLIC ESTERS OF N-HYDROXYALKYLATED IMIDAZOLES

(75) Inventors: Hermann Bergmann, Singapore (SG); Frank Hoefer, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/525,686

(22) PCT Filed: Feb. 11, 2008

(86) PCT No.: PCT/EP2008/051585
§ 371 (c)(1),
(2), (4) Date: Aug. 4, 2009

(87) PCT Pub. No.: WO2008/098886
PCT Pub. Date: Aug. 21, 2008

(65) Prior Publication Data
US 2010/0004462 A1 Jan. 7, 2010

(30) Foreign Application Priority Data

Feb. 15, 2007 (EP) .................................... 07102486
Feb. 21, 2007 (EP) .................................... 07102757

(51) Int. Cl.
*C07D 233/60* (2006.01)
*C07C 69/00* (2006.01)
(52) U.S. Cl. ........................................ 548/341.5; 560/1
(58) Field of Classification Search ............... 548/300.1, 548/341.5; 514/396; 560/1
See application file for complete search history.

(56) References Cited

U.S. PATENT DOCUMENTS

| 2006/0036063 A1 | 2/2006 | Hofer et al. |
| 2007/0123673 A1 | 5/2007 | Hofer et al. |

FOREIGN PATENT DOCUMENTS

| DE | 1 965 308 | 7/1970 |
| DE | 27 25 255 | 12/1977 |
| DE | 27 52 109 | 6/1978 |
| WO | 2006 012980 | 2/2006 |
| WO | 2007 020200 | 2/2007 |
| WO | 2007 051738 | 5/2007 |

OTHER PUBLICATIONS

Patrickios et al, J. Polym. Sci: Part A: Polym Chem. 37 (1999) pp. 1501-1512.*
Patrickios et al, Macromolecular Symposia 171 (2001), pp. 209-224.*
Patrickios et al, Macromolecules 31 (1998), pp. 9075-9077.*
Patrickios et al, Colloids and Surfaces, A: Physiochemical and Engineering Aspects 167 (2000), pp. 61-72.*
Patrickios et al, Polymer (2002), vol. 43(26), pp. 7269-7273.*
*SmithKline Beecham Corporation* v. *Apotex Corporation*. United States Court of Appeals for the Federal Circuit (2006), pp. 1-25.*
Simmons, Martin R. et al., "Synthesis and Aqueous Solution Characterization of Catalytically Active Block Copolymers Containing Imidazole", Macrolmolecules, vol. 31, No. 25, pp. 9075-9077, (1998).
Simmons, Martin R. et al., "Near-Monodisperse, Catalytically Active, Imidazole-Containing Homooligomers: Synthesis by Group Transfer Polymerization and Solution Characterization", Journal of Polymer Science: Part A: Polymer Chemistry, vol. 37, pp. 1501-1512, (1999).
Vamvakaki, Maria et al., "Characterization of Hydrophilic Networks Synthesized by Group Transfer Polymerization", Macromol. Symp., vol. 171, pp. 209-223, (2001).
Patrickios, Costas S. et al., "Synthesis and aqueous solution characterization of catalytically active homopolymers, block copolymers and networks containing imidazole", Coloids and Surfaces, A: Physicochemical and Engineering Aspects., Elsevier, vol. 167, No. 1-2, pp. 61-72, (2000).
U.S. Appl. No. 12/525,826, filed Aug. 5, 2009, Bergmann, et al.
U.S. Appl. No. 12/524,587, filed Jul. 27, 2009, Bergmann, et al.

* cited by examiner

*Primary Examiner* — Joseph Kosack
(74) *Attorney, Agent, or Firm* — Oblon, Spivak, McClelland, Maier & Neustadt, L.L.P.

(57) ABSTRACT

A process for preparing (meth)acrylic esters (F) of N-hydroxyalkylated imidazoles, wherein N-hydroxyalkylated imidazoles (I),

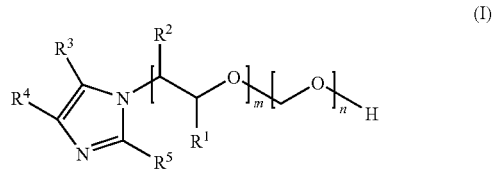

(I)

in which
$R^1$ and $R^2$ may each independently be hydrogen or $C_1$-$C_{20}$-alkyl,
$R^3$, $R^4$ and $R^5$ are each independently hydrogen or $C_1$-$C_{20}$-alkyl, $C_1$-$C_{20}$-alkylcarbonyl, $C_2$-$C_{20}$-alkenyl, $C_2$-$C_{20}$-alkenylcarbonyl, $C_2$-$C_{20}$-alkynyl, $C_2$-$C_{20}$-alkynylcarbonyl, $C_3$-$C_{15}$-cycloalkyl, $C_3$-$C_{15}$-cycloalkylcarbonyl, aryl, arylcarbonyl, a heterocycle or a halogen atom, and
m and n are each integers in the range of in each case from 0 to 20, where m and n cannot simultaneously be 0,
and in which the particular units bracketed by the variables m and n are present in any sequence,
and in which, in the case that m≧2, the $R^1$ and $R^2$ radicals are in each case independent in the particular units,
in the presence of at least one catalyst (K), are esterified with (meth)acrylic acid (S) or transesterified with at least one (meth)acrylic ester (D).

22 Claims, No Drawings

PROCESS FOR PREPARING (METH)ACRYLIC ESTERS OF N-HYDROXYALKYLATED IMIDAZOLES

The present invention relates to a process for catalytically preparing (meth)acrylic esters of N-hydroxyalkylated imidazoles and to their use.

In the context of the present invention, (meth)acrylic acid is understood to mean acrylic acid and/or methacrylic acid; (meth)acrylic esters are understood to mean acrylic esters and/or methacrylic esters. (Meth)acrylic esters are also referred to hereinafter as (meth)acrylates.

(Meth)acrylic esters are prepared usually by acid- or base-catalyzed esterification of (meth)acrylic acid or transesterification of other (meth)acrylic esters with alcohols. Acids or bases are frequently used, such that acid- or base-sensitive (meth)acrylic esters cannot be prepared in a controlled manner by an esterification or transesterification in this way.

Some (meth)acrylic esters of N-hydroxyalkylated imidazoles are known.

The preparation of N-hydroxyethylimidazole methacrylate is described, for example, by Patrickos et al. in various publications (J. Polym. Sci.: Part A: Polym. Chem. 37; 1501-1512 (1999), Macromolecular Symposia 171, 209-224 (2001), Macromolecules 31(25), 9075-9077 (1998), Polymer 43(26), 7269-7273 (2002) and Colloids and Surfaces, A: Physicochemical and Engineering Aspects 167(1-2), 61-72 (2000)). The synthesis of N-hydroxyethylimidazole methacrylate by reacting methacryloyl chloride with N-hydroxyethylimidazole is disclosed therein.

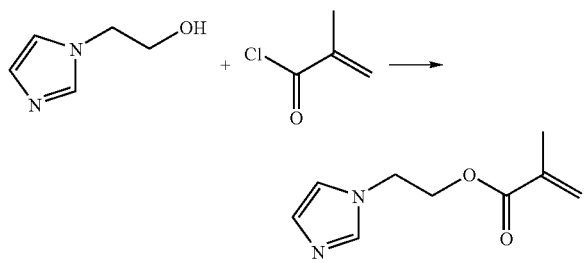

A disadvantage of the synthesis route described therein is the low purity and high APHA color number of the products. This is attributable to factors including the fact that the use of (meth)acryloyl chloride leads to salt formation in the reactions described and, owing to its high reactivity, to unselective reactions, for example Michael additions.

Inst. Chemiefasern, Denkendorf, Fed. Rep. Ger., Chemiefasern/Textilindustrie (1984), 34(6), 428, 420, 433-4, 436-7 describes the preparation of N-hydroxyethylimidazole methacrylate by titanium tetrabutyl-catalyzed ester exchange between the corresponding esters of acetic acid and ethyl methacrylate.

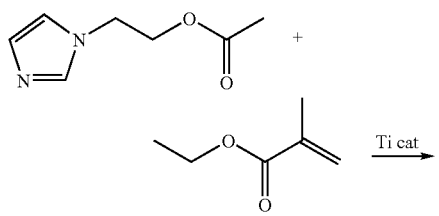

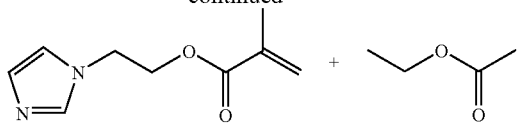

Direct transesterification proceeding from N-hydroxyethylimidazole is not described.

A disadvantage of the processes in the prior art is that the resulting (meth)acrylic esters of N-hydroxyalkylated imidazoles are obtained in poor yields, in low purities and with high color numbers. Moreover, the workup is effected in aqueous medium, which is disadvantageous since the water has to be removed from the product in a complicated manner. Moreover, the processes are uneconomic since the reactants used are expensive.

It was therefore an object of the present invention to provide a further process with which (meth)acrylic esters of N-hydroxyalkylated imidazoles can be prepared from simple reactants in high conversions and high purities. In particular, the resulting (meth)acrylic esters of N-hydroxyalkylated imidazoles should have low color numbers and high purity.

The object was achieved by a process for preparing (meth)acrylic esters (F) of N-hydroxyalkylated imidazoles, in which N-hydroxyalkylated imidazoles (I)

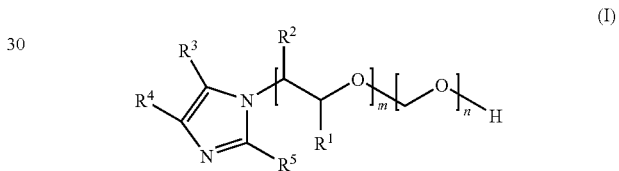

in which
$R^1$ and $R^2$ may each independently be hydrogen or $C_1$-$C_{20}$-alkyl,
$R^3$, $R^4$ and $R^5$ are each independently hydrogen or $C_1$-$C_{20}$-alkyl, $C_1$-$C_{20}$-alkylcarbonyl, $C_2$-$C_{20}$-alkenyl, $C_2$-$C_{20}$-alkenylcarbonyl, $C_2$-$C_{20}$-alkynyl, $C_2$-$C_{20}$-alkynylcarbonyl, $C_3$-$C_{15}$-cycloalkyl, $C_3$-$C_{15}$-cycloalkylcarbonyl, aryl, arylcarbonyl, a heterocycle or a halogen atom, and
m and n are each integers in the range of in each case from 0 to 20, where m and n cannot simultaneously be 0,
and in which the particular units bracketed by the variables m and n are present in any sequence,
and in which, in the case that m≧2, the $R^1$ and $R^2$ radicals are in each case independent in the particular units,
in the presence of at least one catalyst (K), are esterified with (meth)acrylic acid (S) or transesterified with at least one (meth)acrylic ester (D).

Hereinafter, the reactants (meth)acrylic acid (S) and (meth)acrylic ester (D) are also summarized under the term (meth)acrylic compound (B).

With the aid of the process according to the invention, the preparation of (meth)acrylic esters of N-hydroxyalkylated imidazoles is possible with at least one of the following advantages:
use of inexpensive reactants,
high yield,
high purity,
low color numbers, and
no complicated workup (for example removal of water).

Specifically, the collective terms specified for the different R radicals are each defined as follows:

$C_1$-$C_{20}$-Alkyl: straight-chain or branched hydrocarbon radicals having up to 20 carbon atoms, preferably $C_1$-$C_{10}$-alkyl such as methyl, ethyl, propyl, isopropyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methyl-pentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-tri-methylpropyl, 1-ethyl-1-methylpropyl, 1-ethyl-2-methylpropyl, heptyl, octyl, 2-ethylhexyl, 2,4,4-trimethylpentyl, 1,1,3,3-tetramethylbutyl, nonyl or decyl, and isomers thereof.

$C_1$-$C_{20}$-Alkylcarbonyl: a straight-chain or branched alkyl group having from 1 to 20 carbon atoms (as specified above) which is attached via a carbonyl group (—CO—), preferably $C_1$-$C_{10}$-alkylcarbonyl, for example formyl, acetyl, n- or iso-propionyl, n-, iso-, sec- or tert-butanoyl, n-iso-, sec- or tert-pentanoyl, n- or isononanoyl, n-dodecanoyl.

$C_2$-$C_{20}$-Alkenyl: unsaturated, straight-chain or branched hydrocarbon radicals having from 2 to 20 carbon atoms and a double bond in any position, preferably $C_2$-$C_{10}$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trim-ethyl-2-propenyl, 1-ethyl-1-methyl-2-propenyl, 1-ethyl-2-methyl-1-propenyl or 1-ethyl-2-methyl-2-propenyl, and also the isomers of heptenyl, octenyl, nonenyl or decenyl.

$C_2$-$C_{20}$-Alkenylcarbonyl: unsaturated, straight-chain or branched hydrocarbon radicals having from 2 to 20 carbon atoms and a double bond in any position (as specified above), which are attached via a carbonyl group (—CO—), preferably $C_2$-$C_{10}$-alkylcarbonyl, for example ethenoyl, propenoyl, butenoyl, pentenoyl, nonenoyl and isomers thereof.

$C_2$-$C_{20}$-Alkynyl: straight-chain or branched hydrocarbon groups having from 2 to 20 carbon atoms and a triple bond in any position, preferably $C_2$-$C_{10}$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, and also the isomers of heptynyl, octynyl, nonynyl, decynyl.

$C_2$-$C_{20}$-Alkynylcarbonyl: unsaturated, straight-chain or branched hydrocarbon radicals having from 2 to 20 carbon atoms and a triple bond in any position (as specified above), which are attached via a carbonyl group (—CO—), preferably $C_2$-$C_{10}$-alkynylcarbonyl, for example propynoyl, butynoyl, pentynoyl, nonynoyl, decynoyl and isomers thereof.

$C_3$-$C_{15}$-Cycloalkyl: monocyclic saturated hydrocarbon groups having from 3 up to 15 carbon ring members, preferably $C_3$-$C_8$-cycloalkyl such as cyclopropyl, cyclobutyl, cyclopentyl, cyclohexyl, cycloheptyl or cyclooctyl, and a saturated or unsaturated cyclic system, for example norbornyl or norbenzyl.

$C_3$-$C_{15}$-Cycloalkylcarbonyl: monocyclic saturated hydrocarbon groups having from 3 to 15 carbon ring members (as specified above), which are attached via a carbonyl group (—CO—), preferably $C_3$-$C_8$-cycloalkylcarbonyl.

Aryl: a mono- to tricyclic aromatic ring system comprising from 6 to 14 carbon ring members, for example phenyl, naphthyl or anthracenyl, preferably a mono- to bicyclic, more preferably a monocyclic, aromatic ring system.

Arylcarbonyl: preferably a mono- to tricyclic aromatic ring system (as specified above) which is attached via a carbonyl group (—CO—), for example benzoyl, preferably a mono- to bicyclic, more preferably a monocyclic, aromatic ring system.

Heterocycles: five- to twelve-membered, preferably five- to nine-membered, more preferably five- to six-membered, ring systems having oxygen, nitrogen and/or sulfur atoms and optionally a plurality of rings, such as furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

The substituents listed individually may each be interrupted at any position by one or more heteroatoms, where the number of these heteroatoms is not more than 10, preferably not more than 8, even more preferably not more than 5 and in particular not more than 3, and/or may each be substituted at any position, but not more than five times, preferably not more than four times and more preferably not more than three times, by alkyl, alkyloxy, alkyloxycarbonyl, aryl, aryloxy, aryloxycarbonyl, hydroxycarbonyl, aminocarbonyl, heterocycles, heteroatoms or halogen atoms, each of which may likewise be substituted not more than twice, more preferably not more than once, by the groups mentioned.

The compound classes of alkyl, aryl and heterocycles mentioned in this group are each as defined above.

Heteroatoms are oxygen, nitrogen, sulfur or phosphorus.

Alkyloxy is a straight-chain or branched alkyl group which has from 1 to 20 carbon atoms (as specified above) and is attached via an oxygen atom (—O—), preferably $C_1$-$C_{10}$-alkyloxy, for example methoxy, ethoxy, propoxy.

Alkoxycarbonyl is an alkoxy group which has from 1 to 20 carbon atoms (as specified above) and is attached via a carbonyl group (—CO—), preferably $C_1$-$C_{10}$-alkyloxycarbonyl.

Aryloxy is a mono- to tricyclic aromatic ring system (as specified above) which is attached via an oxygen atom (—O—), preferably a mono- to bicyclic, more preferably a monocyclic, aromatic ring system.

Aryloxycarbonyl is a mono- to tricyclic aryloxy group (as specified above) which is attached via a carbonyl group (—CO—), preferably a mono- to bicyclic, more preferably a monocyclic, aryloxycarbonyl.

Halogen atoms are fluorine, chlorine, bromine and iodine.

In the case of the aliphatic substituents mentioned, the $R^3$ and $R^4$ radicals may also be bonded to one another and thus together form a three- to eight-membered, preferably a five- to seven-membered and more preferably a five- to six-membered ring.

In addition, the substituents may each be interrupted at any position by one or more heteroatoms, where the number of these heteroatoms is not more than 10, preferably not more than 8, more preferably not more than 5 and in particular not more than 3. Heteroatoms are oxygen, nitrogen, sulfur or phosphorus.

In a preferred embodiment, the $R^1$ and $R^2$ radicals are each independently hydrogen or $C_1$-$C_{10}$-alkyl, preferably hydrogen or $C_1$-$C_6$-alkyl, and especially preferably hydrogen or $C_1$-$C_4$-alkyl. Most preferably, $R^1$ and $R^2$ are each independently hydrogen or methyl.

In a preferred embodiment, the $R^3$, $R^4$ and $R^5$ radicals are each independently hydrogen or $C_1$-$C_{10}$-alkyl, preferably hydrogen or $C_1$-$C_6$-alkyl, and especially preferably hydrogen or $C_1$-$C_4$-alkyl. Most preferably, $R^3$, $R^4$ and $R^5$ are each hydrogen, methyl or ethyl.

In a particularly preferred embodiment, the $R^3$, $R^4$ and $R^5$ radicals are identical and are each hydrogen, methyl or ethyl.

In another preferred embodiment, m and n are each an integer from 0 to 10, more preferably from 0 to 8 and especially preferably from 0 to 4, where, as mentioned above, M and n cannot simultaneously be 0.

The particular units which are bracketed by the variables m and n may be present in any sequence.

In the case that m≧2, the particular units which are bracketed by the variable m may each bear identical or different $R^1$ and $R^2$ radicals, so that such N-hydroxyalkylated imidazoles (I) comprise ethylene oxide and propylene oxide units in any sequence.

N-Hydroxyalkylated imidazoles (I) suitable in accordance with the invention are monoalkylated imidazoles, for example N-hydroxymethylimidazole and N-hydroxyethylimidazole. Further suitable imidazoles (I) are those which comprise two or more alkoxy units, preferably exactly two alkoxy units. Preferred representatives of this group are imidazoles (I) which comprise two ethoxy or propoxy units.

Particular preference is given to N-hydroxymethylimidazole and N-hydroxyethylimidazole.

When the N-hydroxyalkylated imidazoles (I) are optically active, they are preferably used in racemic form or as a diastereomeric mixture, but it is also possible to use them as pure enantiomers or diastereomers or as enantiomer mixtures.

In the reaction step, the esterification with (meth)acrylic acid (S) or preferably the transesterification of the N-hydroxyalkylated imidazole (I) with at least one, preferably exactly one, (meth)acrylic ester (D) is effected in accordance with the invention in the presence of at least one catalyst (K).

(Meth)acrylic acid (S) can be used for the esterification or (meth)acrylic esters (D) of a saturated alcohol can be used for the transesterification, preferably saturated $C_1$-$C_{10}$-alkyl esters or $C_3$-$C_{12}$-cycloalkyl esters of (meth)acrylic acid, more preferably saturated $C_1$-$C_4$-alkyl esters of (meth)acrylic acid.

In the context of this document, saturated means compounds without C—C multiple bonds (except of course the C=C double bond in the (meth)acryloyl units).

Examples of (meth)acrylic esters (D) are methyl(meth)acrylate, ethyl(meth)acrylate, n-butyl(meth)acrylate, isobutyl(meth)acrylate, tert-butyl(meth)acrylate, n-octyl(meth)acrylate, 2-ethylhexyl(meth)acrylate and cyclohexyl(meth)acrylate, 1,2-ethylene glycol di- and mono(meth)acrylate, 1,4-butanediol di- and mono(meth)acrylate, 1,6-hexanediol di- and mono(meth)acrylate, trimethylolpropane tri(meth)acrylate and pentaerythritol tetra(meth)acrylate.

Particular preference is given to methyl(meth)acrylate, ethyl(meth)acrylate, n-butyl(meth)acrylate and -2-ethylhexyl(meth)acrylate, very particular preference to methyl (meth)acrylate, ethyl(meth)acrylate and n-butyl(meth)acrylate, in particular methyl (meth)acrylate and ethyl(meth)acrylate, and especially methyl(meth)acrylate.

Catalysts (K) usable in accordance with the invention are both heterogeneous and homogeneous catalysts, which may be either acidic or basic.

In the context of this document, heterogeneous catalysts are those which have a solubility in the reaction medium at 25° C. of not more than 1 g/l, preferably of not more than 0.5 g/l and more preferably of not more than 0.25 g/l.

Preference is given to using catalysts (K) which are selected from the group of the (K1) acids,
(K2) Lewis acids,
(K3) alkali metal or alkaline earth metal hydroxides,
(K4) inorganic salts,
(K5) alkali metal bases,
(K6) tertiary nitrogen bases and
(K7) organic tin compounds.

Suitable acidic catalysts (K1) are in principle all acids, irrespective of their acid strength. However, preference is given to those acids which have a $pK_a$ of not more than 7.0, preferably not more than 4.0 and more preferably not more than 1.0. Preference is given to using sulfuric acid, phosphorous acid ($H_3PO_3$), diphosphorous acid ($H_4P_2O_7$), sulfonic acids, more preferably methanesulfonic acid, trifluoromethanesulfonic acid, para-toluenesulfonic acid, benzenesulfonic acid, dodecylbenzenesulfonic acid, cyclododecanesulfonic acid, camphorsulfonic acid or acidic ion exchangers having sulfonic acid groups or mixtures thereof. Zeolites are also conceivable.

In the case of polyprotic acids, the $pK_a$ relates to the first hydrolysis stage.

Suitable Lewis acids (K2) are, for example, metal alkoxides and metal acetylacetonates.

Metal alkoxides are $C_1$-$C_6$-alkoxides, for example methoxides, ethoxides, propoxides, butoxides, pentoxides and hexoxides, and also isomers thereof, of metals such as titanium, zirconium and aluminum. Preferred representatives of this group are titanium tetraisopropoxide (Ti(OiPr)$_4$), titanium tetraisobutoxide (Ti(OiBu)$_4$) and aluminum triisopropoxide (Al(OiPr)$_3$).

Metal acetylacetonates are metal chelates with the enolate anion of 2,4-pentanedione (acetylacetone) and have the general formula $M_n(C_5H_7O_2)_n$ or $M_n(acac)_n$. Useful metals M include numerous metals, especially transition metals. The metals used are preferably aluminum and alkali metals or alkaline earth metals such as lithium, sodium, potassium, magnesium and calcium, preferably sodium and potassium. The transition metals used are preferably titanium, zirconium, chromium, manganese, cobalt, nickel and copper. Preferred representatives of this group are potassium acetylacetonate (K(acac)) and titanium acetylacetonate (Ti(acac)$_4$).

The usable basic catalysts are those having a $pK_B$ of not more than 7.0, preferably not more than 4.0 and more preferably not more than 1.0.

The basic catalysts used are preferably alkali metal hydroxides and/or alkaline earth metal hydroxides (K3).

These may be used either in solid form or in the form of solutions, for example as aqueous solutions.

Suitable alkali metal hydroxides are, for example, lithium hydroxide, sodium hydroxide and potassium hydroxide; suitable alkaline earth metal hydroxides are, for example, magnesium hydroxide and calcium hydroxide. Preference is given to using lithium hydroxide, sodium hydroxide and potassium hydroxide, and also mixtures thereof.

Inorganic salts (K4) usable in accordance with the invention are preferably those which do not exceed the abovementioned limits in the $pK_B$. At the same time, the $pK_B$ should not be below 1.0, preferably not be less than 1.5 and more preferably not be less than 1.6. Inorganic salts (K4) usable in accordance with the invention are preferably heterogeneous inorganic salts.

The inorganic salt (K4) preferably has at least one anion which is selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$) and carboxylate ($R^6$—$COO^-$) in which $R^6$ is $C_1$-$C_{18}$-alkyl, or $C_2$-$C_{18}$-alkyl or $C_6$-$C_{12}$-aryl optionally interrupted by one or more oxygen and/or sulfur atoms and/or one or more substituted or unsubstituted imino groups.

Preference is given to carbonate and phosphate, particular preference to phosphate. Phosphate is also understood to mean the condensation products, for example diphosphates, triphosphates and polyphosphates.

The inorganic salt (K4) has preferably at least one, more preferably exactly one, cation selected from the group consisting of alkali metals, alkaline earth metals, ammonium, cerium, iron, manganese, chromium, molybdenum, cobalt, nickel or zinc.

Preference is given to alkali metals and particular preference to lithium, sodium or potassium.

Particularly preferred inorganic salts (K4) are $Li_3PO_4$, $K_3PO_4$, $Na_3PO_4$, $K_2CO_3$ and $Na_2CO_3$ and also hydrates thereof; very particularly preference is given to $K_3PO_4$. $K_3PO_4$ can, in accordance with the invention, be used in anhydrous form, and also as the tri-, hepta- or nonahydrate.

Alkali metal bases (K5) are understood to mean the alkali metal hydrides and alkali metal salts of $C_1$-$C_6$-alkoxides.

Preference is given to alkali metal hydrides such as lithium hydride, sodium hydride and potassium hydride. Particular preference is given to sodium hydride.

Alkali metal salts of $C_1$-$C_6$-alkoxides are, for example, the lithium, sodium or potassium salts of $C_1$-$C_6$-alkoxides, preferably $C_1$-$C_4$-alkoxides such as methoxide, ethoxide, propoxide and butoxide, and also isomers thereof. Particular preference is given to methoxides and ethoxides, particular preference to methoxides such as sodium methoxide and potassium methoxide.

Tertiary nitrogen bases (K6) are tertiary amines such as trialkylamines, bicyclic amines such as 1,4-diazabicyclo[2.2.2]octane (DABCO) and 1,8-diazabicyclo[5.4.0]undec-7-ene (DBU), and heterocyclic amines such as imidazole, pyridine, pyridazine, pyrimidine and pyrazine; preference is given to DABCO, DBU and pyridine. Suitable trialkylamines are, for example, triethylamine, tributylamine and tribenzylamine. Preference is given to using triethylamine as the tertiary nitrogen base.

Organic tin compounds (K7) are likewise suitable as catalysts. Such compounds are disclosed, inter alia, in DE 2 752 109, DE 1 965 308 and DE 2 725 255. Preferred representatives of this group are dibutyltin laurate and dibutyltin oxide.

Among the catalysts mentioned, suitable catalysts for the esterification of the N-hydroxyalkylated imidazoles (I) with (meth)acrylic acid (S) are especially the acids (K1).

The catalyzed esterification or transesterification is effected generally at from 30 to 140° C., preferably at from 30 to 100° C., more preferably at from 40 to 90° C. and most preferably at from 50 to 80° C.

If appropriate, the reaction can be performed under gentle vacuum of, for example, from 200 hPa to standard pressure, preferably from 200 to 600 hPa and more preferably from 250 to 500 hPa when the water released in the esterification or the low-boiling alcohol formed in the transesterification is to be distilled off, if appropriate as an azeotrope.

The molar ratio between (meth)acrylic acid (S) or (meth)acrylic ester (D) and N-hydroxyalkylated imidazole (I) is, in the case of the esterification or transesterification catalyzed by one of the abovementioned catalysts (K), generally 1-6:1 mol/mol, preferably 1-5:1 mol/mol and more preferably 1-4:1 mol/mol.

The reaction time in the esterification or transesterification catalyzed in accordance with the invention is generally from 45 min to 18 hours, preferably from 2 hours to 12 hours and more preferably from 3 to 10 hours.

The content of catalyst (K) in the reaction medium is generally in the range from about 0.01 to 5 mol %, preferably 0.1-1.8 mol % and more preferably 0.3-1.5 mol %, based on the sum of the N-hydroxyalkylated imidazoles (I) used.

In the esterification or transesterification, polymerization inhibitors (as described below) are absolutely necessary.

The presence of oxygenous gases (see below) during the performance of the process according to the invention is preferred.

In the inventive esterification or transesterification, products having a color number below 500 APHA, preferably below 200 APHA and more preferably below 150 APHA (to DIN ISO 6271) are generally obtained.

The reaction can proceed in organic solvents or mixtures thereof or without addition of solvents. The mixtures are generally substantially anhydrous i.e. the water content is below 10% by weight, preferably below 5% by weight, more preferably below 1% by weight and most preferably below 0.5% by weight. Generally the water content is in a range from 100 to 5000 ppm, preferably 500 to 1000 ppm.

Suitable organic solvents are those monools known for this purpose, for example tertiary monools, such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolan, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and mono- or polyphasic mixtures thereof.

In a particularly preferred embodiment of the transesterification, the reaction is performed in the (meth)acrylic ester (D) used as a reactant. Very particular preference is given to performing the reaction in such a manner that the product (F), after the reaction has ended, is obtained as an about 10-80% by weight solution in the (meth)acrylic ester (D) used as the reactant, especially as a from 20 to 50% by weight solution.

The reactants are present in dissolved form, suspended as solids or in an emulsion in the reaction medium.

The reaction can be effected continuously, for example in a tubular reactor, or in a stirred reactor battery, or batchwise.

The reaction can be performed in all reactors suitable for such a reaction. Such reactors are known to those skilled in the art. Preference is given to effecting the reaction in a stirred tank reactor or a fixed bed reactor.

The reaction mixture can be mixed using any methods. Specific stirrer devices are not required. The mixing can be effected, for example, by feeding in a gas, preferably an oxygenous gas (see below). The reaction medium may be monophasic or polyphasic, and the reactants are dissolved, suspended or emulsified therein. The temperature is adjusted to the desired value during the reaction and can, if desired, be increased or reduced during the course of the reaction.

When the reaction is performed in a fixed bed reactor, the fixed bed reactor is preferably charged with immobilized catalyst (K), in which case the reaction mixture is pumped through a column filled with the catalyst (K). It is also possible to perform the reaction in a fluidized bed reactor, in which case the catalyst (K) is used immobilized on a support. The reaction mixture can be pumped continuously through the column, in which case the flow rate can be used to control the residence time and hence the desired conversion. It is also possible to pump the reaction mixture in circulation through a column, in which case it is also possible to simultaneously distill off the alcohol released under reduced pressure.

The removal of water in the case of an esterification or alcohols which are released from the (meth)acrylic esters (D) in the case of a transesterification is effected continuously or stepwise in a manner known per se, for example by reduced pressure, azeotropic removal, stripping, absorption, pervaporation and diffusion through membranes or extraction.

The stripping can be effected, for example, by passing an oxygenous gas, preferably air or an air-nitrogen mixture, through the reaction mixture, if appropriate in addition to a distillation.

For the absorption, suitable media are preferably molecular sieves or zeolites (pore size, for example, in the range of about 3-10 ångström), or removal by distillation or with the aid of suitable semipermeable membranes.

However, it is also possible to feed the removed mixture of (meth)acrylic ester (D) and its parent alcohol, which frequently forms an azeotrope, directly into a plant for preparing the (meth)acrylic ester (D) in order to reutilize it there in an esterification with (meth)acrylic acid.

After the reaction has ended, the reaction mixture obtained from the esterification or transesterification can be used without further purification or it can, if required, be purified in a further step.

In general, a purification step merely removes the catalyst used from the reaction mixture and the reaction product from any organic solvent used.

A removal of heterogeneous catalysts is effected generally by filtration, electrofiltration, absorption, centrifugation or decantation. The heterogeneous catalyst removed can subsequently be used for further reactions.

The removal of homogeneous catalysts and of the organic solvent is effected generally by distillation, rectification or, in the case of solid reaction products, by filtration.

In the first purification step, however, preference is given to removing only the catalyst and any solvent used.

The reaction mixture which has been purified if appropriate is, if appropriate, subjected to a distillation in which the (meth)acrylic ester (F) of the N-hydroxyalkylated imidazoles is separated by distillation from unconverted (meth)acrylic acid (S) or unconverted (meth)acrylic ester (D), and also any by-products formed.

The distillation units are usually rectification columns of customary design with a circulation evaporator and condenser. The feed is preferably into the bottom region; the bottom temperature here is, for example, 130-160° C., preferably 150-160° C., the top temperature preferably 140-145° C., and the top pressure 3-20 mbar, preferably from 3 to 5 mbar. It will be appreciated that the person skilled in the art can also determine other temperature and pressure ranges in which the particular (meth)acrylic esters (F) of the N-hydroxyalkylated imidazoles can be purified by distillation. What is essential is a separation of the desired product from reactants and by-products under conditions under which the desired product is exposed to a minimum level of degradation reactions.

The distillation unit has generally from 5 to 50 theoretical plates.

The distillation units are of a design known per se and have the customary internals. Useful column internals include in principle all common internals, for example trays, structure packings and/or random packings. Among the trays, preference is given to bubble-cap trays, sieve trays, valve trays, Thormann trays and/or dual-flow trays; among the random packings, preference is given to those comprising rings, helices, saddles, Raschig, Intos or Pall rings, barrel or Intalox saddles, Top-Pak, etc. or braids.

Preference is given to distilling the desired product batchwise, in which case first low boilers are removed from the reaction mixture, usually solvents or unconverted (meth) acrylic acid (S) or (meth)acrylic esters (D). After these low boilers have been removed, the distillation temperature is increased and/or the vacuum is reduced, and the desired product is distilled off.

The remaining distillation residue is usually discarded.

The reaction conditions in the inventive esterification or transesterification are mild. Owing to the low temperatures and otherwise mild conditions, the formation of byproducts in the reaction is prevented, which otherwise, for example, through undesired free-radical polymerization of the (meth) acrylic ester (D) used, which can otherwise be prevented only by addition of stabilizers.

In the inventive reaction, stabilizer can additionally be added to the reaction mixture over and above the storage stabilizer which is present in the (meth)acrylic compound (B) in any case, for example hydroquinone monomethyl ether, phenothiazine, phenols, for example 2-tert-butyl-4-methylphenol, 6-tert-butyl-2,4-dimethylphenol, or N-oxyls such as 4-hydroxy-2,2,6,6-tetramethylpiperidine N-oxyl, 4-oxo-2, 2,6,6-tetramethyl-piperidine N-oxyl or Uvinul® 4040P from BASF Aktiengesellschaft, for example in amounts of from 50 to 2000 ppm. Advantageously, the esterification or transesterification is performed in the presence of an oxygenous gas, preferably air or air-nitrogen mixtures.

The present invention further provides the (meth)acrylic esters (F) obtained by catalytic esterification or transesterification from the N-hydroxyalkylated imidazoles (I).

The (meth)acrylic esters (F) of N-hydroxyalkylated imidazoles (I) prepared in accordance with the invention find use, for example, as monomers or comonomers in the preparation of dispersions, for example acrylic dispersions, as reactive diluents, such as in radiation-curable coating compositions or in paints, and also in dispersions for use in the paper sector, in the cosmetic sector, in the pharmaceutical sector, in agrochemical formulations, in the textile industry and in the sector of oil extraction.

The present invention further provides N-(2'-acryloyl) ethyl)imidazole. This compound is the acrylic ester (F) of an N-hydroxyalkylated imidazole (I) in which m=1, n=0, and $R^1$, $R^2$, $R^3$, $R^4$ and $R^5$ are identical and are each hydrogen.

The examples which follow are intended to illustrate the properties of the invention but without restricting it.

EXAMPLES

"Parts" in this document, unless stated otherwise, refer to "parts by weight".

Example 1

Preparation of Hydroxyethylimidazole Methacrylate by Transesterification with Various Catalysts At a temperature of 65° C., methyl methacrylate (MMA) and hydroxyethylimidazole (HEI) in a molar ratio of 5:1 were heated in the presence of 50 ppm pf phenothiazine, 500 ppm of hydroquinone monomethyl ether and 1.25 mol % of a catalyst (based on hydroxyethylimidazole) for 5 h.

After the end of the reaction time, the mixture was analyzed by gas chromatography. The results are compiled in table 1.

TABLE 1

Transesterification of methyl methacrylate with hydroxyethylimidizole using various catalysts

| Catalyst | HEI [% by wt.] | MMA [% by wt.] | Product of value [% by wt.] |
|---|---|---|---|
| $K_3PO_4$ | 6.4 | 80.7 | 11.8 |
| $K_2CO_3$ | 9.3 | 83.9 | 6.2 |
| NaOH | 8.9 | 84.3 | 6.4 |
| LiOH | 9.4 | 85.2 | 5.1 |
| K(acac) | 6.2 | 82.1 | 11.0 |
| $Zr(acac)_4$ | 6.9 | 82.0 | 10.8 |
| $NaOCH_3$ | 8.3 | 81.0 | 9.7 |
| dibutyltin laurate | 13.1 | 85.2 | 0.6 |
| $(Bu)_2SnO$ | 12.0 | 87.2 | 0.0 |
| $Ti(OiPr)_4$ | 12.2 | 87.5 | 0.0 |
| $Ti(OiBu)_4$ | 12.6 | 84.6 | 0.0 |
| p-toluenesulfonic acid | 13.0 | 86.5 | 0.0 |
| $H_2SO_4$ | 11.9 | 87.7 | 0.0 |

It can be seen that, in all cases, the transesterification did not lead to full conversion, since the methanol formed was not removed under the experimental conditions.

It was found that various catalysts such as $K_3PO_4$, $K_2CO_3$, NaOH, LiOH, K(acac), $Zr(acac)_4$ and $NaOCH_3$ are very suitable for the transesterification of methyl methacrylate with hydroxyethylimidazole.

Example 2

Preparation of Hydroxyethylimidazole Methacrylate by Transesterification with Potassium Phosphate as the Catalyst Potassium phosphate was employed as the catalyst for the reaction of a larger scale. The transesterification was effected in a 750 ml Miniplant reactor with Oldershaw column and liquid distributor. The reflux ratio was 25:1 (reflux:efflux), the stirrer speed (anchor stirrer) was 400 rpm and the air introduction was 1.5 l/h.

This apparatus was initially charged with 195 mg of hydroquinone monomethyl ether (350 ppm), 28 mg of phenothiazine (50 ppm), 436 g (4.36 mol) of methyl methacrylate (MMA) and 122 g (1.09 mol) of hydroxyethylimidazole, which were stirred. Subsequently, 4.63 g (22 mmol; 2.0 mol % based on hydroxyethylimidazole) of anhydrous potassium phosphate were added, the vacuum was established (300 mbar) and the suspension was heated (the jacket temperature was adjusted to 120° C. by means of thermostating). After approx. 20 minutes, the suspension began to boil; this time was selected as the start point (t=0 min). During the reaction, distillate was removed continuously and the temperature in the bottom rose up to 75° C. After 300 min, the reaction was ended and the vacuum was broken. The suspension was cooled and then filtered through a pressure suction filter (30 ml of MMA were added subsequently to flush the residue).

306 g of crude product were obtained, which were distilled with air introduction. This initially removed the excess MMA. Subsequently, 400 ppm of Kerobit® BPD (BASF Aktiengesellschaft, N,N'-di-sec-butyl-p-phenylenediamine) were added for stabilization and the product of value was obtained by distillation at 133° C. and 1.3 mbar.

162 g (82% yield) of hydroxyethylimidazole methacrylate were obtained in a high purity of 98% (GC analysis) as a clear, slightly yellowish liquid. The APHA color number was 54.

Example 3

Preparation of Hydroxyethylimidazole Acrylate by Transesterification with Various Catalysts At a temperature of 60° C., methyl acrylate (MA) and hydroxyethylimidazole (HEI) in a molar ratio of 5:1 were heated in the presence of 50 ppm of phenothiazine, 500 ppm of hydroquinone monomethyl ether and 1.25 mol % of a catalyst (based on hydroxyethylimidazole) for 5 h.

After the end of the reaction time, the mixture was analyzed by gas chromatography. The results are compiled in table 2.

TABLE 2

Transesterification of methyl acrylate with hydroxyethylimidizole using various catalysts

| Catalyst | HEI [% by wt.] | MA [% by wt.] | By-product [% by wt.] | Product of value [% by wt.] |
|---|---|---|---|---|
| $K_3PO_4$ | 3.4 | 71.1 | 16.2 | 7.9 |
| $K_2CO_3$ | 8.5 | 72.1 | 10.6 | 7.6 |
| NaOH | 10.8 | 76.0 | 6.1 | 5.8 |
| K(acac) | 3.2 | 70.7 | 17.5 | 6.9 |
| $Zr(acac)_4$ | 10.0 | 76.2 | 0.2 | 10.0 |
| $NaOCH_3$ | 14.4 | 79.9 | 2.4 | 1.7 |
| $Ti(OiPr)_4$ | 15.4 | 81.2 | 1.4 | 0.7 |
| $Ti(OiBu)_4$ | 13.7 | 82.4 | 1.0 | 0.7 |
| $Al(OiPr)_3$ | 16.8 | 74.9 | 2.0 | 0.0 |
| p-toluene-sulfonic acid | 20.9 | 73.4 | 1.6 | 1.0 |
| $H_2SO_4$ | 15.5 | 73.2 | 0.8 | 0.3 |
| DABCO[1] | 15.5 | 78.3 | 1.2 | 0.5 |
| DBU[2] | 6.6 | 72.5 | 10.4 | 7.5 |
| NaH | 14.9 | 76.5 | 2.7 | 1.4 |
| triethylamine | 16.8 | 77.6 | 1.7 | 1.0 |
| pyridine | 16.1 | 77.7 | 1.5 | 0.4 |

[1]DABCO = 1,4-diazabicyclo[2.2.2]octane
[2]DBU = 1,8-diazabicyclo[5.4.0]undec-7-ene It can be seen that, in all cases, the transesterification did not lead to full conversion, since the methanol formed was not removed under the experimental conditions.

Consequently, the by-product, according to GC-MS analyses, was the 1,4 addition product of methanol to hydroxyethylimidazole acrylate:

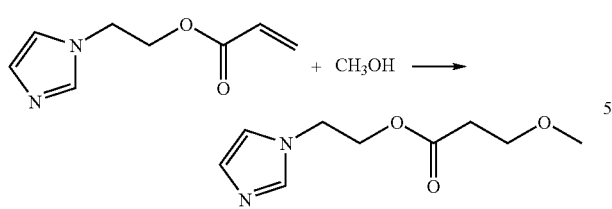

Only when Zr(acac)$_4$ was used was a very small amount of by-product formed, since this catalyst virtually completely suppresses this side reaction.

It was found that various catalysts such as K$_3$PO$_4$, K$_2$CO$_3$, NaOH, K(acac), Zr(acac)$_4$ and DBU are very suitable for the transesterification of methyl acrylate with hydroxyethylimidazole.

Example 4

Preparation of Hydroxyethylimidazole Acrylate by Transesterification with Zirconium Acetylacetonate (Zr(acac)$_4$) as the Catalyst Zirconium acetylacetonate was employed as the catalyst for the reaction on a larger scale. The transesterification was effected in a 750 ml miniplant reactor with Oldershaw column and liquid distributor. The reflux ratio was 25:1 (reflux:efflux), the stirrer speed (anchor stirred) was 400 rpm and the air introduction was 1.5 l/h.

This apparatus was initially charged with 170 mg of hydroquinone monomethyl ether (350 ppm), 24 mg of phenothiazine (50 ppm), 384 g (4.46 mol) of methyl acrylate (MA) and 50 g (0.45 mol) of hydroxyethylimidazole, which were stirred. Subsequently, 8.7 g (17.8 mmol; 4.0 mol % based on hydroxyethylimidazole) of zirconium acetylacetonate were added, the vacuum was established (300 mbar) and the suspension was heated (the jacket temperature was adjusted to 100° C. by means of thermostating). After approx. 15 minutes, the suspension began to boil; this time was selected as the start point (t=0 min). During the reaction, distillate was removed continuously and the temperature in the bottom rose up to 56° C. After 300 min, the reaction was ended and the vacuum was broken. The suspension was cooled and then filtered through a pressure suction filter (30 ml of MA were added subsequently to flush the residue).

185 g of crude product were obtained, which, according to GC analyses, comprised 41% by weight of hydroxyethylimidazole acrylate, 0.5% by weight of hydroxyethylimidazole and 53% by weight of methyl acrylate.

A portion of the crude product was purified by column chromatography. Hydroxyethylimidazole methacrylate was obtained in a high yield of >96% (GC analysis) as a clear colorless liquid.

The product was analyzed by means of $^1$H and $^{13}$C NMR and also mass spectrometry:

$^1$H NMR (500 MHz, d$_6$-DMSO): δ=7.69 (s, 1H), 7.21 (s, 1H), 6.94 (s, 1H), 6.32 (d, 1H), 6.17 (dd, 1H), 5.95 (d, 1H), 4.36-4.40 (m, 2H), 4.31-4.27 (m, 2H).

$^{13}$C NMR (125 MHz, d$_6$-DMSO): δ=165.1 (s), 137.6 (d), 131.9 (t), 128.5 (d), 127.9 (d), 119.5 (d), 63.6 (t), 45.0 (t).

MS (EI), m/z (%): 166 (25) [M$^+$], 111 (4) [M$^+$-COCHCH$_2$], 94 (100) [M$^+$-HO(CO)CHCH$_2$], 81 (30), 67 (10), 55 (70) [COCHCH$_2$].

The invention claimed is:

1. A process for preparing a (meth)acrylic ester of an N-hydroxyalkylated imidazole, the process comprising esterifying an N-hydroxyalkylated imidazole of formula (I)

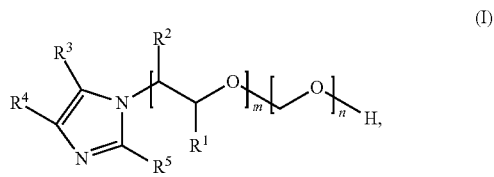

in which
R$^1$ and R$^2$ are each independently hydrogen or C$_1$-C$_{20}$-alkyl,
R$^3$, R$^4$ and R$^5$ are each independently hydrogen or C$_1$-C$_{20}$-alkyl, C$_1$-C$_{20}$-alkylcarbonyl, C$_2$-C$_{20}$-alkenyl, C$_2$-C$_{20}$-alkenylcarbonyl, C$_2$-C$_{20}$-alkynyl, C$_2$-C$_{20}$-alkynylcarbonyl, C$_3$-C$_{15}$-cycloalkyl, C$_3$-C$_{15}$-cycloalkylcarbonyl, aryl, arylcarbonyl, a heterocycle or a halogen atom, and
m and n are each integers in a range of in each case from 0 to 20, where m and n cannot simultaneously be 0,
and in which the particular units bracketed by the variables m and n are present in any sequence,
and in which, in the case that m≧2, R$_1$ and R$_2$ are in each case independent in the particular units,
in the presence of at least one catalyst,
with (meth)acrylic acid or
transesterifying said N-hydroxyalkylated imidazole with at least one (meth)acrylic ester of a saturated alcohol.

2. The process according to claim 1, wherein R$^1$ and R$^2$ are each independently hydrogen or C$_1$-C$_{10}$-alkyl.

3. The process according to claim 2, wherein R$^1$ and R$^2$ are each independently hydrogen or methyl.

4. The process according to claim 1, wherein R$^3$, R$^4$ and R$^5$ are each independently hydrogen or C$_1$-C$_{10}$-alkyl.

5. The process according to claim 4, wherein R$^3$, R$^4$ and R$^5$ are identical and are each hydrogen, methyl or ethyl.

6. The process according to claim 1, wherein m and n are each an integer from 0 to 10.

7. The process according to claim 1, wherein the N-hydroxyalkylated imidazole is at least one member selected from the group consisting of a monoalkylated imidazole and an imidazole having two or more alkoxy units.

8. The process according to claim 1, wherein the N-hydroxylated imidazole is N-hydroxymethylimidazole or N-hydroxyethylimidazole.

9. The process according to claim 1, wherein the N-hydroxylated imidazole is at least one selected from the group consisting of an imidazole having two ethoxy units and an imidazole having two propoxy units.

10. The process according to claim 1, wherein the catalyst is at least one selected from the group consisting of
an acid,
a Lewis acid,
an alkali metal or alkaline earth metal hydroxide,
an inorganic salt,
an alkali metal base,
a tertiary nitrogen, and
an organic tin compound.

11. The process according to claim 1, wherein the catalyst comprises at least one acid having a pK$_a$ of not more than 7.0.

12. The process according to claim 1, wherein the catalyst comprises at least one Lewis acid selected from the group consisting of a metal C$_1$-C$_6$-alkoxide and a metal acetylacetonate.

13. The process according to claim 12, wherein the Lewis acid is at least one selected from the group consisting of titanium tetraisopropoxide ($Ti(OiPr)_4$), titanium tetraisobutoxide ($Ti(OiBu)_4$), aluminum triisopropoxide ($Al(OiPr)_3$), potassium acetylacetonate (K(acac)), and titanium acetylacetonate ($Ti(acac)_4$).

14. The process according to claim 1, wherein the catalyst comprises at least one alkali metal or alkaline earth metal hydroxide selected from the group consisting of lithium hydroxide, sodium hydroxide, and potassium hydroxide.

15. The process according to claim 1, wherein the catalyst comprises at least one inorganic salt comprising at least one anion which is selected from the group consisting of carbonate ($CO_3^{2-}$), hydrogencarbonate ($HCO_3^-$), phosphate ($PO_4^{3-}$), hydrogenphosphate ($HPO_4^{2-}$), dihydrogenphosphate ($H_2PO_4^-$), sulfate ($SO_4^{2-}$), sulfite ($SO_3^{2-}$), and a carboxylate ($R^6$—$COO^-$) in which $R^6$ is $C_1$-$C_{18}$-alkyl, or $C_2$-$C_{18}$-alkyl, or $C_6$-$C_{12}$-aryl, optionally interrupted by one or more oxygen and/or sulfur atoms and/or one or more substituted or unsubstituted imino groups.

16. The process according to claim 1, wherein the catalyst comprises at least one inorganic salt comprising at least one cation selected from the group consisting of an alkali metal, an alkaline earth metal, ammonium, cerium, iron, manganese, chromium, molybdenum, cobalt, nickel, and zinc.

17. The process according to claim 1, wherein the catalyst comprises at least one inorganic salt selected from the group consisting of $Li_3PO_4$, $K_3PO_4$, $Na_3PO_4$, $K_2CO_3$, a hydrate of $Li_3PO_4$, a hydrate of $K_3PO_4$, a hydrate of $Na_3PO_4$, and a hydrate of $K_2CO_3$.

18. The process according to claim 1, wherein the (meth) acrylic ester of a saturated alcohol is a saturated $C_1$-$C_{10}$-alkyl ester.

19. The process according to claim 1, wherein the (meth) acrylic ester of a saturated alcohol is selected from the group consisting of methyl (meth)acrylate, ethyl (meth)acrylate, n-butyl (meth)acrylate, and 2-ethylhexyl (meth)acrylate.

20. 2-(1H-imidazol-1-yl)ethyl acrylate.

21. The process according to claim 1, wherein the catalyst comprises at least one inorganic salt comprising at least one anion which is a carboxylate ($R^6$—$COO^-$) in which $R^6$
   is $C_6$-$C_{12}$-aryl, and
   is interrupted by at least one selected from the group consisting of an oxygen atom, a sulfur atom, a substituted imino group, and an unsubstituted imino group.

22. The process according to claim 1, wherein the catalyst comprises at least one inorganic salt comprising at least one anion which is a carboxylate ($R^6$—$COO^-$) in which $R^6$
   is $C_2$-$C_{18}$-alkyl, and
   is interrupted by at least one selected from the group consisting of an oxygen atom, a sulfur atom, a substituted imino group, and an unsubstituted imino group.

* * * * *